(12) United States Patent
Gower et al.

(10) Patent No.: US 7,090,868 B2
(45) Date of Patent: Aug. 15, 2006

(54) MATERIALS AND METHODS FOR DRUG DELIVERY AND UPTAKE

(75) Inventors: Laurie A. Gower, Gainesville, FL (US); Vishal M. Patel, Gainesville, FL (US); Piyush Sheth, Baltimore, MD (US); Allison Gallup, Jacksonsville, FL (US); Michael Ossenbeck, Gainesville, FL (US)

(73) Assignee: University of Florida, Gainesville, FL (US)

( * ) Notice: Subject to any disclaimer, the term of this patent is extended or adjusted under 35 U.S.C. 154(b) by 96 days.

(21) Appl. No.: 10/243,340

(22) Filed: Sep. 13, 2002

(65) Prior Publication Data

US 2004/0052865 A1 Mar. 18, 2004

(51) Int. Cl.
*A61K 9/14* (2006.01)

(52) U.S. Cl. ............... 424/489; 424/490; 424/450; 424/686

(58) Field of Classification Search ............ 424/400, 424/450, 458, 489, 490, 686
See application file for complete search history.

(56) References Cited

U.S. PATENT DOCUMENTS

| | | | |
|---|---|---|---|
| 4,110,267 A | 8/1978 | Ikeda et al. | |
| 4,464,317 A | 8/1984 | Thies et al. | |
| 5,030,391 A | 7/1991 | Sumita et al. | |
| 5,756,210 A | 5/1998 | Dupuis et al. | |
| 5,811,126 A | 9/1998 | Krishnamurthy | |
| 5,916,596 A | 6/1999 | Desai et al. | |
| 6,159,504 A * | 12/2000 | Kumabe | 424/489 |
| 6,225,361 B1 | 5/2001 | Nakajima | |
| 6,309,663 B1 | 10/2001 | Patel et al. | |
| 2001/0003594 A1 | 6/2001 | Watanabe et al. | |
| 2002/0058732 A1* | 5/2002 | Mistry et al. | 523/201 |

FOREIGN PATENT DOCUMENTS

WO WO 94/01001 A1 1/1994
WO WO 03/089022 A1 10/2003

OTHER PUBLICATIONS

Dictionary.com definition of "film". Accessed Jul. 25, 2005. 1 page.*
Bruinsma, P.J. et al. "Mesoporous Silica Synthesized by Solvent Evaporation: Spun Fibers and Spray-Dried Hallow Spheres" *Chem. Mater.*, 1997, 9:2507-2512.
Caruso. F. "Hollow Capsule Processing through Colloidal Templating and Self-Assembly" *Chem. Eur. J.*, 2000. 6(3):413-419.
Cölfen. H. and M. Antonietti "Crystal Design of Calcium Carbonate Microparticles Using Double-Hydrophilic Block Copolymers" *Langmuir*, 1998, 14:582-589.
Enomae, T. "Application of Hollow Calcium Carbonate Particles to Papermaking" *Proceedings of the 5th Asian Textile Conference*, Oct. 2, 1999, 1:464-467.
Gower, L. "The Influence of Polyaspartate Additive on the Growth and Morphology of Calcium Carbonate Crystals" Doctoral Dissertation, 1997, University of Massachusetts at Amherst.
Gower, L. et al. "Synthesis of Calcium Carbonate Coated Emulsions Droplets for Drug Detoxification" Poster Materials presented at the Particles conference in Orlando. FL on Apr. 21, 2002.
Gower, L. and D. Odom "Deposition of calcium carbonate films by a polymer-induced liquid-precursor (PILP) process" *J Crystal Growth*. 2000, 210:719-734.
Hirai, T. and I. Komasawa "Preparation and microscopic structure control of fine particle materials by using emulsion liquid membrane system as microreactor" *Kagaku Kogaku Ronbunshu*. May 2001. 27(3):303-313 (English abstract).
Hirai, T. et al. "Biomimetric Synthesis of Calcium Carbonate Particles in a Pseudovesicular Double Emulsion" *Langmuir*. 1997. 13:6650-6653.
Iida, M. et al. "Titanium Dioxide Hollow Microspheres with an Extremely Thin Shell" *Chem Mater.*, 1998. 10:3780-3782.
Kawahashi, N. and E. Matijevic "Preparation of Hallow Spherical Particles of Yttrium Compounds" *J. Colloid Interface Sci.*, Apr. 1991, 143(1):103-110.
Lee, I. et al. "Nanoparticle-Directed Crystallization of Calcium Carbonate" *Adv. Mater.*, Nov. 2. 2001. 13(21):1617-1620.
Lowenstam, H.A. and S. Weiner "Minerals and Macromolecules"0 in *On Biomineralization*, Oxford University Press: New York, 1989. pp. 7-24.
Nogami, M. et al. "Fabrication of hollow glass microspheres in the $Na_2-B_2O_3-SiO_2$ system from metal alkoxides" *J. Mater. Sci.*, 1982. 17:2845-2849.

(Continued)

*Primary Examiner*—Leon B. Lankford, Jr.
*Assistant Examiner*—Lora E Barnhart (57) ABSTRACT

The subject invention pertains to novel materials and methods for use in delivering and sequestering substances, such as pharmacological agents, within a patient. One aspect of the invention is directed towards core-shell particles having a core encapsulated within a calcium carbonate shell, with an intermediate layer composed of an amphiphilic compound surrounding the core. When the particles of the subject invention are administered to a patient, they are capable of removing lipophilic drugs by absorption of the drug through their mineral shell and into their core. The particles of the subject invention can also be administered to a patient as controlled release, drug delivery vehicles. Thus, in another aspect, the subject invention concerns a method of delivering pharmacological agents by administering the core-shell particles of the subject invention to a patient in need of such administration.

35 Claims, 5 Drawing Sheets

OTHER PUBLICATIONS

Patel, V. et al. "Synthesis of Calcium Carbonate Coated Emulsion droplets for Drug Detoxification" Poster Materials presented at the American Chemical Society Meeting in Orlando, FL on Apr. 7-11, 2002.

Pekarek, K.H. et al. "Double-walled polymer microspheres for controlled drug release" *Nature.* Jan. 20, 1994, 367:258-260.

Putlitz, B. et al. "The Generation of "Armored Latexes" and Hollow Inorganic Shells Made of Clay Sheets by Templating Cationic Miniemulsions and Latexes" *Adv. Mater.*, Apr. 4. 2001, 13(7)500-503.

QI, L. et al. "Biomimetic Morphogenesis of Calcium Carbonate in Mixed Solustion of Surfactants and Double-Hydrophillic Block Copolymers" *Adv. Mater..* Feb. 19, 2002, 14(4):300-303.

Underhill, R.S. et al. "Alkoxysilane Microemulsions with Skin Layers for use in Drug Detoxification" *Abstracts of Papers of the American Chemical Society.* Apr. 1-5. 2001. 221st ACS National Meeting, Abstract No. 545.

Walsh, D. and S. Mann "Fabrication of hollow porous shells of calcium carbonate from self-organizing media" *Nature,* Sep. 28, 1995. 377:320-323.

Walsh, D. et al. "Morphosynthesis of Calcium Carbonate (Vaterite) Microsponges" *Adv. Mater.*, 1999. 11(4):324-328.

Wilcox, D.L. and M. Berg "Microsphere Fabrication and Applications: An Overview" *Mat. Res. Soc. Symp. Proc.*, 1995, 372:3-313.

Zhong, Z. et al. "Preparation of Mesoscale Hollow Spheres of $TiO_2$ and $SnO_2$ by Templating Against Crystalline Arrays of Polystyrene Breads" *Adv. Mater.* 2000, 12(3):206-209.

U.S. Appl. No. 10/418,843, filed Apr. 18, 2003, Gower et al.

Davey, R.J. and T. Hirai "The preparation of calcium carbonate in an emulsifiled liquid membrane" *J. Crys. Grow.*, 1997, 171:318-320.

Hirai, T. et al. "Preparation of $Gd_2O_3$: $Eu^{3+}$ and $Gd_2O_2S$ : $Eu^{3+}$ Phosphor Fine Particles Using an Emulsion Liquid Membrane System" *J. Coll. Inter. Sci.*, 2002, 253:62-69.

Hirai, T. et al. "Preparation of $Y_2O_3$: $Eu^{3+}$ phosphor fine particles using an emulsion liquid membrane system" *J. Mater. Chem.*, 2000, 10:2306-2310.

Hirai, T. et al. "The Preparation of Spherical Calcium Phosphate Fine Particles Using an Emulsion Liquid Membrane System" *Langmuir*, 2000. 16:955-960.

Hirai, T. et al. "The Preparation of Spherical Bioceramic Fine Particles Reinforced by Alumina Using an Emulsion Liquid Membrane System" *Langmuir*, 2000, 16:8213-8216.

Hirai, T. et al. " Preparation of Acicular Ferrite Fie Particles Using an Emulsion Liquid Membrane System" *Langmuir*, 1999, 15:6291-6298.

Hirai, T. et al. "Preparation of Composite Sr-Pb Oxalate Fine Particles Using an Emulsion Liquid Membrane System" *J. Chem. Eng. Jpn.*, 1998, 31(5):787-794.

Hirai, T. et al. "Preparation of Rare Earth Oxalate Ultrafine Particles Using an Emulsion Liquid Membrane System Using Carboxylic Acid as Cation Carrier" *J. Chem. Eng. Jpn.*, 1998, 31(3):474-477.

Hirai, T. et al. "Preparation of Spherical Oxalate Particles of Rare Earths in Emulsion Liquid Membrane System" *AIChE J.*, Jan. 1998, 44(1):197-206.

Hirai, T. et al. "Preparation of Rare-Earth-Metal Oxalate Spherical Particles in Emulsion Liquid Membrane system Using Alkyphosphinic Acid as Cation Carrier" *Langmuir*, 1998,14:6648-6653.

Hirai, T. et al. "Preparation of Copper Oxalate Fine Particles usig Emulsion Liquid Membrane System" *J. Chem. Eng. Jpn.*, 1996, 29(5):842-850.

Konishi, Y. et al. "Precipitation Stripping of Yttrium Oxalate Powders from Yttrium-Loaded Carboxylate Solutions with Aqueous Oxalic Acid Solutions" *Ind. Eng. Chem. Res.*, 1998, 37:2093-2098.

Konishi, Y. et al. "Characterization of Neodymium Oxalate Precipitated from 2-Ethylhexyl Phosphonic Acid Mono-2-Ethylhexyl Ester Solution" *Metallurgical Trans. B*, Jun. 1993, 24B:537-539.

Konishi, Y. et al. "Precipitation Stripping of Neodymium from Carboxylate Extractant with Aqueous Oxalic Acid Solutions" *Ind. Eng. Chem. Res.*, 1993, 32:937-942.

Majima, H. et al, "Preparation of Monisized Ultrafine Particles of Precious Metals Utilizing an Emulsion-Type Liquid Membrane Technique" *Metallurgical Trans. B*, Aug. 1991, 22B:397-404.

Mann, S. "The Chemistry of Form" *Angew. Chem. Int. Ed.*, 2000, 39:3392-3406.

Mann, S. "Molecular tectonics in biomineralization and biomimetic materials chemistry" *Nature*, Oct. 7, 1993. 365:499-505.

Mann, S. et al. "Controlled crystallization of $CaCO_3$under stearic acid monolayers" *Nature.* Aug. 1988, 334:692-365.

Teramoto, M. et al. "Extraction of Lanthanoids by Liquid Surfactant Membranes" *Sep. Sci. Technol.*, 1986, 21(3):229-250.

Teramoto, M. et al. "Modeling of the Permeation of Copper through Liquid Surfactant Membranes" *Sep. Sci. Technol.*, 1983, 18(8):735-764.

Yang, M. et al. "The precipitation of solids in a liquid membrane emulsion: the control of particle size" *Powder Tech.*, 1991, 65:235-242.

U.S. Appl. No. 10/819,040, filed Apr. 5, 2004, Gower et al.

U.S. Appl. No. 10/243,340, filed Sep. 13, 2002, Gower et al.

Gower, L. et al. "The influence of templates on mineralization via a precursor process"presented Aug. 12, 2002 at Gordon Research Conference (GRC), New London, New Hampshire.

Gower, L. et al. "Biomimetic bone" presented at ACERS 28th Int. Cocoa Beach Conference on Advanced Ceramics and Composites, Jan. 28, 2004, Cocoa Beach, FL.

Gower, L. "Biomimetic processing of ceramic composites" presented at CIMTEC—10th International Ceramics Congress and 3rd Forum on New Materials, Jul. 14-18, 2002, Florence, Italy.

Gower, L. "A new paradigm for biomineral formation" presented at 7th Int. Conf.—The Chemistry and Biology of Mineralized Tissues, Nov. 4-9, 2001, Sawgrass, FL.

Olszta, M.J. et al. "Synthesis of nano-fibrous $CaCO_3$ through a solution-precursor-solid (SPS) process" presented Apr. 7, 2003 at Materials Research Society (MRS) Spring Meeting, San Francisco, California.

Olszta, M.J. and L. Gower "Biomimetic composites using a polymer-induced liquid-precursor (PILP) process" presented Jun. 2002 at Annual Society for Experimental Mechanics (SEM) meeting, Milwaukee, Wisconsin.

Olszta, M.J. et al. "Scanning electron microscopic analysis of the mineralization of type I collagen via a polymer-induced liquid-precursor (PILP) process" *Calcif. Tissue Int.*, 2003, 72(5):583-591, Epub date Mar. 6, 2003.

Olszta, M.J. "Biomimetic mineralization of type-I collagen" presented at 7th Int. Conf.—The Chemistry and Biology of Mineralized Tissues, Nov. 4-9, 2001, Sawgrass, FL.

Olszta, M.J. et al. "Mimicking the nanostructured architecture of bone" presented at Fall Materials Research Society (MRS), Session L: Continuous Nanophase and Nanostructured Materials, Dec 1-5, 20003, Boston, MA.

Olszta, M.J. "Biomimetic mineralization of type-I collagen" presented at UEF Biomimetic Engineering Conference, Mar. 3-7, 2002, Destin, FL.

Olszta, M.J. et al. "Biomimetic mineralization of type I collagenous matrices" presented at MRS Spring Meeting Proceedings, Symposium O-Materials Inspired by Biology, Apr. 21-25, 2003, San Francisco, CA.

Addadi, L. and S. Weiner "Control and Design and Principles in Biological Mineralization" *Angew. Chem. Int. Ed. Engl.* 1992, 31:153-169.

Addadi, L. et al. "A Chemical Model for the Cooperation of Sulfates and Carboxylates in Calcite Crystal Nucleation: Reievance to Biomineralization" *PNAS USA*, May 1, 1987, 84(9):2732-2736.

Addadi, L. et al. "Growth and Dissolution of Organic Crystals with 'Tailor-Made' Inhibitors—Implications in Stereochemistry and Materials Science" *Angew. Chem. Int. Ed. Engl.*, 1985, 24:466-485.

Addadi, S. and S. Weiner "Interactions between Acidic Proteins and Crystals: Stereochemical Requirements in Biomineralization" *PNAS USA*, Jun. 15, 1985, 82 (12):4110-4114.

Aizenberg, J. "Patterned crystallization of calcite in vivo and in vitro" *J. Crystal Growth*, 2000, 211:143-148.

Gower, L. and D. Tirrell "Calcium carbonate films and helices grown in solutions of poly(aspartate)" *J. Crystal. Growth*, 1998, 191:153-160.

Greenfield, E.M. et al. "Ionotropic Nucleation of Calcium Carbonate by Molluscan Matrix" *Amer. Zool.*, 1984, 24:925-932.

Olszta, M.J. et al., "A New Paradigm for Biomineral Formation: Mineralization via an Amorphous Liquid-Phase Precursor" *Connective Tissue Res.*, 2003. 4(Suppl. 1): 326-334.

Olszta, M. "Biomimetic Mineralization of Collagen for Nanostructured Composites" poster materials, Jun. 2001, Department of Materials Science and Engineering, University of Florida, Gordon Research Conference.

Sivakumar, M. and Panduranga Rao "Preparation, characterization and in vitro release of gentamicin from coralline hydroxyapatite-gelatin composite microspheres" *Biomaterials*, 2002, 23:3175-3181.

* cited by examiner

MATERIALS AND METHODS FOR DRUG DELIVERY AND UPTAKE

The subject invention was made with government support under a research project supported by National Science Foundation Grant No. EEC-9402989. The government has certain rights in this invention.

BACKGROUND OF THE INVENTION

Treatment of drug overdose in humans, whether due to therapeutic miscalculation, illicit drug use, or suicide attempt, presents a major problem to the health care industry worldwide. In the United States alone, over 300,000 patients are admitted to the emergency rooms because of drug overdose. Treatment of these patients costs the healthcare industry over ten billion dollars because of hospital expenses and lost employee productivity. This does not include the $80 billion associated with alcohol abuse (Moudgil, B. M., *Seventh Year Annual Report*. 2001: Engineering Research Center for Particle Science and Technology, University of Florida).

Current treatment protocols for overdosed patients vary with the drug of concern, but are focused on three objectives: prevention of drug absorption, enhancement of drug excretion, and administration of pharmacological antidotes. The first two are accomplished with techniques nonspecific to the ingested drug, such as emesis, gastric lavage, or use of activated charcoal for the former objective, and dialysis or hemoperfusion for the latter. However, since absorption of toxic drugs is very time sensitive, and since these techniques are applied only once a patient reaches the emergency room, they are not as effective as would be desired, with some techniques reported to recover only 30% of the ingested drug (Rumack, B. H., *Poisoning: Prevention of absorption, in Poisoning and Overdose*, M. J. Bayer and B. H. Rumack, Eds., 1983, p. 13–18). There also currently exist very few specific pharmacological antidotes to the drugs frequently associated with life threatening overdose cases (Moudgil, B. M., *Seventh Year Annual Report*. 2001: Engineering Research Center for Particle Science and Technology, University of Florida).

An important factor influencing drug distribution in the body is the ability of toxins to bind to blood proteins and tissues. Certain tissues have strong binding affinities for specific toxins, causing localized concentration in that tissue. This is true especially of the kidney and liver, because of their metabolic and excretory functions. Some toxins bind noncovalently to albumin, a blood plasma protein, or other proteins. While bound to protein, the complex becomes pharmacologically inert and is trapped in the bloodstream due to its large size. Only unbound drugs are able to cross lipoprotein membranes and exert an effect. A drug's free molecule concentration is likely to increase during an overdose, since protein-binding sites are more readily saturated. Therefore, it is expected that a patient with low levels of albumin will experience higher toxicity effects than a patient with normal levels (Lu, F., *Basic Toxicology: Fundamentals, Target Organs, and Risk Assessment*. 3rd ed. 1996, Taylor and Francis: Washington; Fenton, J. J., *Toxicology: A Case-Oriented Approach*. 2002, CRC Press: Boca Raton; Stine, K. E. and T. M. Brown, *Principles of Toxicology*. 1996, CRC Press: Boca Raton).

Micron-scale and nano-scale core-shell particulate systems, either hollow or fluid-filled, have become of recent interest. Core-shell particles find important applications in encapsulation of a variety of materials for catalysis and controlled release applications (e.g. drugs, enzymes, pesticides, dyes, etc.); for use as filler in lightweight composites, pigment, or coating materials; and in biomedical implant materials (Putlitz, B. Z. et al., *Adv. Mater.*, 2001, 13:500-+; Walsh, D. and Mann, S., *Nature*, 1995, 377:320–323; Walsh, D. et al., *Adv. Mater.*, 1999, 11:324–328; Zhong, Z. et al., *Adv. Mater.*, 2002, 12:206–209; Caruso, F., *Chem.-Eur. J.*, 2000, 6:413–419).

Recently, the use of particulate systems as a treatment for patients overdosed on lipophilic drugs has been proposed (Moudgil, B. M., *Seventh Year Annual Report*. 2001: Engineering Research Center for Particle Science and Technology, University of Florida). Several particulate systems, including microemulsions, polymer microgels, silica nanotubes and nanosponges, and silica core-shell particles, are currently being investigated for this detoxification purpose. It has been proposed that, when intravenously administered to an overdosed patient, such particles will effectively detoxify the patient's circulatory system of the particular lipophilic toxin by either: (a) absorption, from the selective partitioning of the drug molecules from the blood to the hydrophobic core of the particle; or (b) adsorption of the drug molecules onto surfaces of surface-functionalized particles. Furthermore, in order to catalyze the toxin metabolism, and hence its removal from the blood, the immobilization of toxin-specific catabolic enzymes on or within particles is being pursued (Moudgil, B. M., *Seventh Year Annual Report*. 2001: Engineering Research Center for Particle Science and Technology, University of Florida).

Fabrication of hollow sphere particles has been accomplished using various methods and materials. In general, three fabrication classes are currently employed: sacrificial cores, nozzle reactor systems, and emulsion or phase separation techniques (Caruso, F., *Chem.-Eur. J.*, 2000, 6:413–419; Wilcox, D. L. and Berg, M., in *Materials Research Society*, 1994, Boston: Materials Research Society). The first involves the coating of a core substrate with a material of interest, followed by the removal of the core by thermal or chemical means. In this manner, hollow particles of yttrium compounds (Kawahashi, N. and Matijevic, E., *J Colloid Interface Sci.*, 1991, 143:103–110), $TiO_2$ and $SnO_2$ (Zhong, Z. et al., *Adv. Mater.*, 2002, 12:206–209), and silica (Caruso, F., *Chem.-Eur. J.*, 2000, 6:413–419) have been synthesized. Nozzle reactor systems make use of spray drying and pyrolysis, and their use has successfully led to the fabrication of hollow glass (Nogami, M. et al., *J. Mater. Sci.*, 1982, 17:2845–2849), silica (Bruinsma, P. J. et al., *Chem. Mater.*, 1997, 9:2507–2512), and $TiO_2$ (Iida, M. et al., *Chem. Mater.*, 1998, 10:3780) particles. Emulsion-mediated procedures, or hollow particle synthesis, is a third common method. This has been used to form latex (Putlitz, B. Z. et al., *Adv. Mater.*, 2001, 13:500-+), polymeric (Pekarek, K. J. et al., *Nature*, 1994, 367:258–260), and silica core-shell particles (Underhill, R. S. et al., *Abstracts of Papers of the American Chemical Society*, 2001, 221:545).

Calcium carbonate coated core-shell particles have also been synthesized. By coating polystyrene beads with calcium carbonate, followed by removal of the polymer core, hollow particles in the 1 μm to 5 μm size range have been generated (Walsh, D. and Mann, S., *Nature*, 1995, 377: 320–323; U.S. Pat. No. 5,756,210). Core-shell particles have also been synthesized using water-in-oil (Walsh, D. et al, *Adv. Mater.*, 1999, 11:324–328; Enomae, T., *Proceedings of the 5$^{th}$ Asian Textile Conference*, 1999, 1:464–467), and water-in-oil-in-water (Hirai, T. et al, *Langmuir*, 1997, 13:6650–6653; Hirai, T. and Komasawa, I., *Kagaku Kogaku Ronbunshu*, 2001, 27:303–313) emulsions as templates for calcium carbonate nucleation. In other processes, Lee et al. (Lee, I. et al., *Adv. Mater.*, 2001, 13:1617–1620) and Qi et al. (Qi, L. M. et al., *Adv. Mater.*, 2002, 14:300) respectively use monolayer-protected gold particles and double-hydrophilic block copolymer (DHBC)-surfactant complex micelles as templates for calcium carbonate deposition, resulting in core-shell particles up to 5 μm in diameter.

Some of the calcium carbonate core-shell systems discussed in the scientific literature are generated by using a biomimetic process (Walsh, D. and Mann, S., *Nature*, 1995, 377:320–323; Walsh, D. et al., *Adv. Mater.*, 1999, 11:324–328; Hirai, T. et al., *Langmuir*, 1997, 13:6650–6653; Hirai, T. and Komasawa, I., *Kagaku Kogaku Ronbunshu*, 2001, 27:303–313; Qi, L. M. et al., *Adv. Mater.*, 2002, 14:300). Mineralization in biological systems has been the focus of intense research because their successful mimicry has important implications for the synthetic design of superior materials. Exquisite control of mineral deposition in biosystems is thought to occur partly due to the presence of an insoluble organic matrix, along with modulation of the crystal growth process via soluble macromolecular species, such as acidic proteins and polysaccharides (Lowenstam, H. A. and Weiner, S., *On Biomineralization*, Oxford University Press: New York, 1989).

As can be understood from the above, there remains a need for a particulate system that is capable of neutralizing or eliminating toxic levels of drugs within a patient in a short period of time, and which can be produced with the high degree of control associated with biomimetic processes.

BRIEF SUMMARY OF THE INVENTION

The subject invention pertains to novel materials and methods for use in delivering and segregating substances, such as pharmacological agents, within a patient. One aspect of the invention is directed towards particles having a core encapsulated by a solid calcium carbonate shell, with an intermediate layer of amphiphilic molecules surrounding the core. When the particles of the subject invention are administered to a patient, they are capable of removing lipophilic drugs by absorption of the drug through their porous mineral shell and into their core. In one embodiment, the core of the particles is hollow. In another embodiment, the core contains a fluid, which is preferably an oil. The particles of the subject invention can also be administered to a patient as drug delivery vehicles. Thus, in another aspect, the subject invention concerns a method of delivering or sequestering pharmacological agents by administering the calcium carbonate-encapsulated particles of the subject invention to a patient in need of such administration.

The particles of the subject invention can be designed with various porosities, in order to effectively absorb or release a selected substance over a period of time.

In another aspect, the subject invention concerns a method for making the calcium carbonate core-shell particles of the subject invention by using a polymer-induced liquid-precursor (PILP) process.

BRIEF DESCRIPTION OF THE DRAWINGS

FIGS. 1A–1C show reactants and resulting core-shell particles of the subject invention.

DETAILED DISCLOSURE OF THE INVENTION

The subject invention concerns particles having a core contained within a solid calcium carbonate shell, with an intermediate layer of amphiphilic molecules surrounding the core. The subject invention also concerns a method of producing the calcium carbonate-encapsulated particles by templating a porous calcium carbonate shell onto the surface of oil-in-water emulsion droplets using a polymer-induced liquid precursor (PILP) process. In another aspect, the subject invention pertains to methods for sequestering lipophilic agents within a patient by administering an effective amount of the core-shell particles to the patient.

Briefly, the particles of the present invention can be produced by blending an oil, such as n-dodecane, with water and an amphiphile, the latter acting as a surfactant to stabilize the droplets within water, forming emulsion droplets. The resultant emulsion droplets can then be introduced into solutions of $CaCl_2$, $MgCl_2$, and a short-chained acidic polymer additive (such as polyaspartic acid). A $CO_3^{2-}$ counter ion is then introduced into the mixture, such as by slow peristaltic pumps, thereby producing calcium carbonate coated particles that can then be centrifuged and dried.

The particles can be constructed in sizes suitable for particular applications, such as micro-scale or nano-scale particles. For example, the process of the subject invention can produce particles, such as microspheres, having a calcium carbonate shell within the range of about 1 μm to about 200 μm in diameter. In another embodiment, the shell has a diameter within the range of about 1 μm to about 50 μm in diameter. In yet another embodiment, the shell has a diameter within the range of about 1 μm to about 5 μm in diameter. In order to pass through the circulatory system of the body, smaller particles can be constructed having a diameter within the range of about 100 nm to about 300 nm, for example, using microemulsion templates.

Advantageously, the method of the subject invention can produce particles having a shell of uniform thickness. Preferably, the calcium carbonate shell has a thickness within the range of about 100 nm to about 1000 nm in thickness. The core-shell particle of claim 1, wherein said shell has a thickness within the range of about 200 nm to about 500 nm in thickness.

The particles of the subject invention are biodegradable and can be administered to patients for sequestration of a pharmacological agent (drug uptake) following an overdose, as a detoxification agent. Detoxification can occur through several mechanisms. Once administered into a patient (e.g., via the circulatory system), the particles can absorb a lipophilic drug into their oily core, or adsorb the drug through dipole/charge interactions with the mineral shell.

Optionally, drug-degrading enzymes, such as P450 enzymes, can operate within the particles, or be coated onto or otherwise associated with the surface of the particles. In another embodiment, the particles can release enzymes that degrade the drug into harmless catabolites. The calcium carbonate shell provides stabilization to the emulsion, and operates as a molecular screen or filter, to avoid saturation of the particles with proteins and other lipophilic species in the blood, for example. The particles of the subject invention can also be administered to a patient as drug delivery vehicles, such as controlled release drug delivery vehicles, which could occur through either pores templated into the shell, or via degradation of the shell.

Preferably, the particles are of nano-scale dimensions and non-aggregating, to avoid blockage of blood capillaries (if administered into the circulatory system), and are biocompatible (e.g., non-thrombogenic). If the particles are not sufficiently small to pass through the blood-renal barrier, a biodegradable material can be included for gradual removal of the particulates from the blood stream (at a rate slow enough for the body to tolerate the gradual release of the absorbed toxin). Optionally, environment-sensitive catabolic enzymes for catalysis of the target drug are immobilized within the particles; in which case, the synthesis can be accomplished under benign processing conditions.

The subject invention also concerns a method of producing the calcium carbonate-encapsulated particles of the subject invention using a polymer-induced liquid-precursor (PILP) process. Using the novel and facile method of the subject invention, calcium carbonate "hard" shell—"soft" core particles can be synthesized under benign conditions. The method of the subject invention utilizes an oil-in-water emulsion droplet as a template. The procedure relies on the surface-induced deposition of a calcium carbonate mineral precursor on to emulsion droplets by a polymer-induced liquid-precursor (PILP) process, elicited by including short-chained highly acidic polymers, such as polyaspartic acid, into crystallizing solutions of calcium carbonate which are slowly raised in supersaturation. The deposition of thin films of calcium carbonate onto glass coverslips using the PILP process has been demonstrated, as described previously (Gower, L. B. and Odom, D. J., *J. Cryst. Growth*, 2000, 210:719–734). In those studies, in situ observations revealed that the acidic polymer transforms the solution crystallization process into a precursor process by inducing liquid-liquid phase separation in the crystallizing solution. Droplets of a liquid-phase mineral precursor can be deposited onto various substrates in the form of a film or coating, which upon solidification and crystallization, produces a continuous mineral film that maintains the morphology of the precursor phase (hence, the name precursor). Using the method of the subject invention, the PILP process is utilized to coat an oil droplet in solution, generating a fluid-filled core-shell particle with a thin uniform shell of calcium carbonate. In some cases, the precursor phase may not appear to be a liquid, but instead have solid-like characteristics (e.g. glassy). In either case, the important aspect is that both are an amorphous precursor phase, which due to coalescence during the formation of the phase, lead to a smooth continuous coating of mineral rather than the traditional solution crystallization of three-dimensional crystallites. It has also been found that the inhibitory action of Mg-ion can lead to a similar precursor process, and in the presence of surfactant, polymer may not be necessary, although optimal conditions include a combination of Mg-ion and polymer.

The process of the subject invention can be carried out under a variety of conditions. For example, in the case of an aqueous system, the process can be carried out at a temperature of about 4° C. to about 28° C. For ease of processing, the process can be carried out at room temperature (about 23° C.). The process is preferably carried out at a pH within the range of about 7 to about 11 and at 1 atm. More preferably, the process is carried out at a pH of about 11. However, the process can be carried out at a pH lower than 7 or higher than 11 provided a surfactant is utilized that remains charged at the particular pH. Preferably, the oil:water ratio is within the range of about 1:8 and about 1:10, by volume. More preferably, the oil:water ratio is about 1:9, by volume.

Using the process of the subject invention, the diameter of the particles can be controlled. For example, the diameter of the particles can be increased by increasing the size of the emulsion droplet from which the particles are formed. Vesicular types of particles (such as unilamellar or multilamellar liposomes) are feasible as well, which could be used to fabricate core-shell particles with an aqueous interior surrounded by the mineral shell. For example, in preparing the particles, a liposome could be substituted for the emulsion droplet as a template, which would then be exposed to the amorphous mineral precursor. This could increase the potential number of applications to include encapsulated agents that require an aqueous environment, such as water soluble molecules and macromolecules, biopolymers (e.g. proteins, DNA) and cells.

Using the process of the subject invention, the calcium carbonate shell porosity can be controlled. Because the highly PILP phase will preferentially deposit on charged or polar regions of patterned substrates, it is possible to pattern porosity into the mineral shell by using an organic template with hydrophobic domains. For example, increased porosity can be obtained by increasing the quotient of surfactant with uncharged head groups (such as cholesterol or diolein) in the mixture of surfactants used to stabilize the emulsion droplet.

One or more of a variety of short-chained acidic polymers can be utilized to initiate the amorphous liquid-phase mineral precursor, including different polymers and biological materials. As used herein, the term "short-chained acidic polymer" is intended to mean oligomeric-length scale polymers bearing at least one acidic functionality on one or more monomers of the polymer chain. Polyacrylic acid (PAA), polymethacrylates (PMA), sulfonated polymers, phosphorylated peptides and polymers, sulfated glycoproteins, polyaspartic acid, polyglutamic acid, and copolymers of these materials can be utilized to induce the liquid-phase separation, for example. A range of polymer molecular weights can be suitable if the other variable of the crystallizing conditions are appropriately modified to generate the PILP phase.

Unlike those particles reported previously, using the method of the subject invention allows one to generate a smooth and uniform shell of calcium carbonate around the oil droplet, and not an aggregation of individual crystals, as is common among the previously published work. Furthermore, in this manner, oil can be encapsulated within the particle, leading to a "soft" fluidic core—a feature that is advantageous (although not necessary) for the effective extraction of lipophilic molecules from aqueous media by an absorption mechanism.

Preferably, the shell of the particle of the subject invention is composed of magnesium-bearing calcium carbonate and is at least 80% calcium carbonate. More preferably, the shell is composed of at least 90% calcium carbonate. The Mg-ion is added as an additional inhibitory agent (to eliminate traditional solution crystallization), and potentially other ions or molecules could serve this function, in combination with the polymer.

The core of the core-shell particle is a void containing a compound in the oil phase that is incompatible with water. Preferably, the compound in the oil phase is a hydrophobic compound, such as an oil. More preferably, the hydrophobic compound is an organic compound having a solubility to water of not more than 1 gram per 10 grams of water at 20° C. For example, one or more of a variety of oils, such as dodecane or hexadecane, can be incorporated within each particle, occupying its hollow core. Other organic compounds that can be utilized include, but are not limited to, cyclohexane, n-hexane, benzene, cottonseed oil, rapeseed oil, squalane, squalene, waxes, styrene, divinylbenzene, butyl acrylate, 2-ethylhexyl acrylate, cyclohexyl acryalate, decyl acrylate, lauryl acrylate, dodecenyl acrylate, myristyl acrylate, palmityl acrylate, hexadecenyl acrylate, stearyl acrylate, octadecenyl acrylate, behenyl acrylate, butyl methacrylate, 2-ethylhexyl methacrylate, cyclohexyl methacrylate, decyl methacrylate, lauryl methacrylate, dodecenyl methacrylate, myristyl methacrylate, palmityl methacrylate, hexadecenyl methacrylate, stearyl methacrylate, octadecenyl methacrylate, behenyl methacrylate, silicone macromonomers, and the like.

Particles can be loaded with a selected substance or substances, such as a biologically active agent, by contact with a solution containing the agent. In one embodiment, the biologically active agent, such as a detoxifying enzyme, is incorporated within the emulsion droplet during formation of the core-shell particle. Loading can be carried out by adding the biologically active agent to the oil phase prior to emulsification and coating of the droplet, for example. Because detoxifying enzymes are typically oil soluble, they can be readily captured into the oil-in-water emulsion prior to encapsulation with the mineral shell.

In another aspect, the subject invention pertains to a method of sequestering a lipophilic agent within a patient by administering an effective amount of core-shell particles to the patient, wherein the core-shell particles absorb the lipophilic agent through their calcium carbonate shell and into their oil core. The particles can be administered through any of a variety of routes known in the art, including enteral and parenteral, such as intravenous. Preferably, the particles are administered into the circulatory system of the patient, via a blood vessel, such as a vein or artery. The patient may be suffering from overdose, wherein a toxic concentration of the lipophilic agent is present within the patient, such as in the bloodstream. The patient may also be suffering from harmful drug interaction between the lipophilic agent and another lipophilic agent or non-lipophilic agent.

In another aspect, the subject invention pertains to a method of delivering a biologically active agent to a patient by administering an effective amount of core-shell particles containing a selected biologically active agent to the patient, wherein the core-shell particles can release the biologically active agent within the patient. The particles can be administered through any of a variety of routes known in the art, including enteral, pulmonary, and parenteral, such as intravenous. Preferably, the particles are administered into the circulatory system of the patient, such as through a blood vessel.

The particles of the subject invention can be administered using any of a variety of means known in the art. For example, administration of an effective amount of particles can include the injection of the particles in a blood vessel, such as an artery.

Following administration of the particles and drug release or drug sequestration, the spent particles can, optionally, be retrieved from the patient using a variety of methods. For example, if the particles are not sufficiently biodegradable, they can be filtered from the blood, such as in a dialysis process.

The term "biodegradable", as used herein, means capable of being biologically decomposed. A biodegradable material differs from a non-biodegradable material in that a biodegradable material can be biologically decomposed into units which may be either removed from the biological system and/or chemically incorporated into the biological system.

The term "biocompatible", as used herein, means that the material does not elicit a substantial detrimental response in the patient. It should be appreciated that when a foreign object is introduced into a living body, that the object may induce an immune reaction, such as an inflammatory response that can have negative effects on the patient. As used herein, the term "biocompatible" is intended to include those materials that cause some inflammation, provided that these effects do not rise to the level of pathogenesis.

The particles of the subject invention can be used as a vehicle for the delivery of biologically active agents, such as medical substances in the field of therapeutics. The active agents may be incorporated in the oil-containing core or chemically bonded to the calcium carbonate shell, for example.

As used herein, the terms "incorporated within" or "otherwise associated with" mean that the particular agent is contained within the particle of the subject invention or is directly or indirectly bound to the particle in some fashion. For example, the biologically active agent can be contained within the oil core of the particle, or operate as a component of the calcium carbonate shell or amphiphilic layer. The biologically active agent can be "free" or bonded to any of the other components of the particle. The particular agent can be incorporated within, or otherwise associated with, the particles of the subject invention, during or subsequent to production of the particles. For example, a biologically active agent, such as an enzyme, can be attached to the outer shell through direct adsorption or through a linker molecule. Alternatively, the agent can be physically entrapped in the mineral phase, as it is deposited, and subsequently released upon degradation of the mineral.

The biologically active agents that can be delivered using the particles of the subject invention can include, without limitation, medicaments, vitamins, mineral supplements, substances used for the treatment, prevention, diagnosis, cure or mitigation of disease or illness, substances which affect the structure or function of the body, or drugs. The active agents include, but are not limited to, antifungal agents, antibacterial agents, anti-viral agents, anti-parasitic agents, growth factors, angiogenic factors, anaesthetics, mucopolysaccharides, metals, cells, antibodies, antibody fragments, and other agents. Because the processing conditions can be relatively benign, live cells can be incorporated into the particles during their formation, or subsequently allowed to infiltrate the particles through tissue engineering techniques.

The terms "pharmaceutically active agent", "biologically active compound", "biologically active agent", "active agent", "active compound" and "drug" are used herein interchangeably and include pharmacologically active substances that produce a local or systemic effect in a human or non-human animal. The terms thus mean any substance intended for use in the diagnosis, cure, mitigation, treatment or prevention of disease or in the enhancement of desirable physical or mental development and conditions in a human or non-human animal.

Examples of antimicrobial agents that can be delivered using the particles of the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

Growth factors that can be incorporated into or otherwise associated with the particles of the present invention include, but are not limited to, basic fibroblast growth factor (bFGF), acidic fibroblast growth factor (aFGF), nerve growth factor (NGF), epidermal growth factor (EGF), insulin-like growth factors 1 and 2 (IGF-1 and IGF-2), platelet-derived growth factor (PDGF), tumor angiogenesis factor (TAF), vascular endothelial growth factor (VEGF), corticotropin releasing factor (CRF), transforming growth factors alpha and beta (TGF-α and TGF-β), interleukin-8 (IL-8), granulocyte-macrophage colony stimulating factor (GM-CSF), bone morphogenic protein (BMP), the interleukins, and the interferons.

Other agents that can be incorporated into or otherwise associated with the particles of the subject invention include acid mucopolysaccharides including, but not limited to, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin.

Proteins that can be incorporated into or otherwise associated with the particles of the subject invention include, but are not limited to, collagen (including cross-linked collagen), fibronectin, laminin, elastin (including cross-linked elastin), osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, platelet derived growth factor and skeletal growth factor, or combinations and fragments thereof.

Other biologically active agents that can be incorporated into or otherwise associated with the particles of the subject invention include genetically-modified or non-genetically modified cells. Thus, the particles of the subject invention can contain such cells within their core and be administered to a patient. The cells can be non-stem cells (mature and/or specialized cells, or their precursors or progenitors) or stem cells. Thus, the cells can range in plasticity from totipotent or pluripotent stem cells (e.g., adult or embryonic), precursor or progenitor cells, to highly specialized or mature cells, such as those of the pancreas. In one embodiment, the cells are genetically modified to produce a biologically active agent, such as a detoxifying enzyme.

Stem cells can be obtained from a variety of sources, including fetal tissue, adult tissue, cord cell blood, peripheral blood, bone marrow, and brain, for example. Stem cells and non-stem cells (e.g., specialized or mature cells, and precursor or progenitor cells) can be differentiated and/or genetically modified. Methods and markers commonly used to identify stem cells and to characterize differentiated cell types are described in the scientific literature (e.g., Stem Cells: Scientific Progress and Future Research Directions, Appendix E1-E5, report prepared by the National Institutes of Health, June, 2001). The list of adult tissues reported to contain stem cells is growing and includes bone marrow, peripheral blood, brain, spinal cord, dental pulp, blood vessels, skeletal muscle, epithelia of the skin and digestive system, cornea, retina, liver, and pancreas.

The active agents incorporated within, or otherwise associated with, the particles of the subject invention can exhibit modified release characteristics. Release of the active agent can be controlled using a variety of methods. For example, biologically decomposable conjugates can be utilized. Alternatively, release of the active agent can be controlled by inserting the active agent in various components of the particle that have a different biodegradability. For example, if used in medical or agricultural applications, it may be desired to be able to control the release dosage and release rate of active agents. In one embodiment, the particles exhibit a decreasing (decaying) rate of release (first-order release kinetics). In another embodiment, the particles exhibit a constant rate of release (zero-order release kinetics). In another embodiment, the particles exhibit one or more sudden releases, or bursts, after a certain delay time.

The particles of the subject invention can be utilized to administer hormones, for example. An important field of application is the development of therapeutic systems for the controlled release of an anti-diabetic agent, such as insulin, in the treatment of pancreatic diabetes. The particles of the subject invention can also be utilized to administer anti-tumor compounds, such as cytotoxic agents, for the treatment of cancer.

Larger micro-scale particles of the invention can contain cells. According to the methods of the invention, such particles can be utilized to deliver the cells, and/or active agents produced by the cells, in vivo. Examples of cells that can be incorporated within, or otherwise associated with, the particles of the subject invention include, but are not limited to, stem cells, precursor or progenitor cells, chondrocytes, pancreatic cells, hepatocytes, and neural cells. Such cells can be released from the particles upon degradation of the shell in vivo.

The surface of the particles can be modified using surface modification methods known to those of ordinary skill in the art. For example, the amphiphilic layer composition can be varied to vary the uncharged head group domain size.

As used herein, the term "lipophilic" is intended to mean oil soluble. Examples of lipophilic drugs include amitriptyline, bupivicaine, and amiodarone.

As used herein, the term "oil" is intended to mean any nonpolar, water-insoluble compound.

As used herein, the terms "amphiphile" "amphiphilic compound", and "surfactant" are used herein interchangeably and intended to mean a compound having at least one hydrophilic (polar) portion and at least one hydrophobic (nonpolar) portion, such as stearic acid and arachidic acid. Typically, amphiphiles exhibit amphiphilic behavior in which their molecules become concentrated at the interface between a polar solvent and a nonpolar solvent. Preferably, the amphiphilic compounds used in the subject invention have molecules with at least one hydrophilic head group and at least one hydrophobic tail. More preferably, the amphiphilic compound has a partially deprotonated carboxylic acid headgroup functionality.

The particles of the subject invention can be formulated in any of a variety of forms or shapes in the micro- or nano-scale size range (e.g., microparticles or nanoparticles).

The particles of the present invention can be, for example, capsules (e.g., microcapsules or nanocapsules), or spheres (e.g., microspheres or nanospheres).

The core-shell particles of the subject invention can be formulated and administered as a pharmaceutical composition, containing a pharmaceutically acceptable carrier or diluent. The pharmaceutical compositions of the subject invention can be formulated according to known methods for preparing pharmaceutically useful compositions. Formulations are described in a number of sources which are well known and readily available to those skilled in the art. For example, Remington's Pharmaceutical Science (Martin E W [1995] Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules, vials, and disposable syringes made of glass or plastic, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that, in addition to the ingredients particularly mentioned above, the formulations of the subject invention can include other agents conventional in the art having regard to the type of formulation in question. The pharmaceutical compositions can be included in a container, pack, or dispenser, together with instructions for administration.

The particles of the subject invention can be applied as a film or coating on a substrate. The substrate can be composed of any material, such as metal, polymer, and/or ceramic materials.

The term "patient", as used herein, refers to any vertebrate species. Preferably, the patient is of a mammalian species. Mammalian species which benefit from the disclosed methods of drug delivery and/or detoxification include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales.

The particles of the subject invention can be used in novel therapeutic systems in which ferrous components are associated with the particles so as to impart magnetic properties to the particles. The magnetic properties of the particles can induce and control the release of the active agent via a "magnetic switch" that may be operated from outside the body. In some therapeutic approaches, systems of particles and active agents can be selectively accumulated in their target area using external magnetic fields. For treating very special problems, small magnets can be implanted within the patient for local control in the target area, e.g., a tumor area.

The particles of the subject invention are useful in diagnostic applications, as well. For example, the particles of the subject invention can incorporate, or otherwise be associated with, visualization markers, and are applicable for many special indications such as magnetic resonance (MR) lymphography after intravenous or local interstitial administration, tumor visualization, visualization of functions or malfunctions, of plaque (atherosclerosis imaging), thrombi and vascular occlusions, MR angiography, perfusion imaging, infarct visualization, visualization of endothelial damages, receptor imaging, visualization of blood-brain barrier integrity, etc., as well as for differential diagnosis, in particular, for distinguishing tumors/metastases from hyperplastic tissue.

The particles are also useful for industrial applications, such as use as light-weight pigment/filler particles or as platelets for high contrast print gloss.

The terms "comprising", "consisting of", and "consisting essentially of" are defined according to their standard meaning and may be substituted for one another throughout the instant application in order to attach the specific meaning associated with each term.

Material and Methods

Emulsion Substrate Synthesis. Oil-in-water emulsion droplets were synthesized by blending in a household kitchen blender, n-dodecane oil (SIGMA-ALDRICH) and distilled water in 1:9 volume ratio, stabilized with 1% w/v stearic acid (SIGMA-ALDRICH) (per oil phase volume). The distilled water was adjusted to the desired pH using 0.01M NaOH (FISHER SCIENTIFIC) prior to emulsification.

Particle Synthesis. Immediately after preparing the emulsion, as indicated above, 1 mL of the emulsion was pippetted into 35 mm FALCON polystyrene petri dishes, followed by 1 mL of an 80 mM/400 mM $CaCl_2/MgCl_2$ solution (SIGMA-ALDRICH) (freshly prepared using distilled water, and filtered by 0.2 μm ACRODISC syringe filters). Next, 36 μL of a freshly prepared and filtered 1 mg/mL solution of poly-(α,β)-D,L-aspartic acid (MW 8600) (ICN/SIGMA-ALDRICH) was transferred to each petri dish by micropipet. The petri dishes were then covered by parafilm, which was punched with a small hole, into which the outflow end of the tubing from an ultra-low flow peristaltic pump (FISHER SCIENTIFIC) was inserted. At a rate of approximately 0.025 mL/min, 2 mL of a freshly prepared and filtered solution of 300 mM $(NH_4)_2CO_3$ (SIGMA-ALDRICH) was pumped into each petri dish (taking about 80 minutes to complete). The resulting product was collected and centrifuged at 8000 rpm for 10 minutes, rinsed with saturated $CaCO_3$ (SIGMA-ALDRICH), then re-centrifuged under the same conditions. After a rinsing with ultrapure ethanol (FISHER SCIENTIFIC), the product was re-centrifuged a final time under the same conditions, and then left to dry in air overnight.

Determination of Particle Morphology and Composition. The dried particles were examined by an OLYMPUS BX60 polarized light microscope, using a gypsum wave-plate in order to observe both amorphous and crystalline phases. For scanning electron microscopy (SEM) observations, particle samples were spread onto aluminum studs, and then gold-coated and examined with a JEOL 6400 SEM. Energy Dispersive Spectroscopy (EDS) was used for elemental composition analysis of the particle shell. For diffraction studies, dried particles were adhered to double-sided tape, and analyzed in a PHILIPS APD 3720 X-ray instrument.

EXAMPLE 1

Figure 1A:
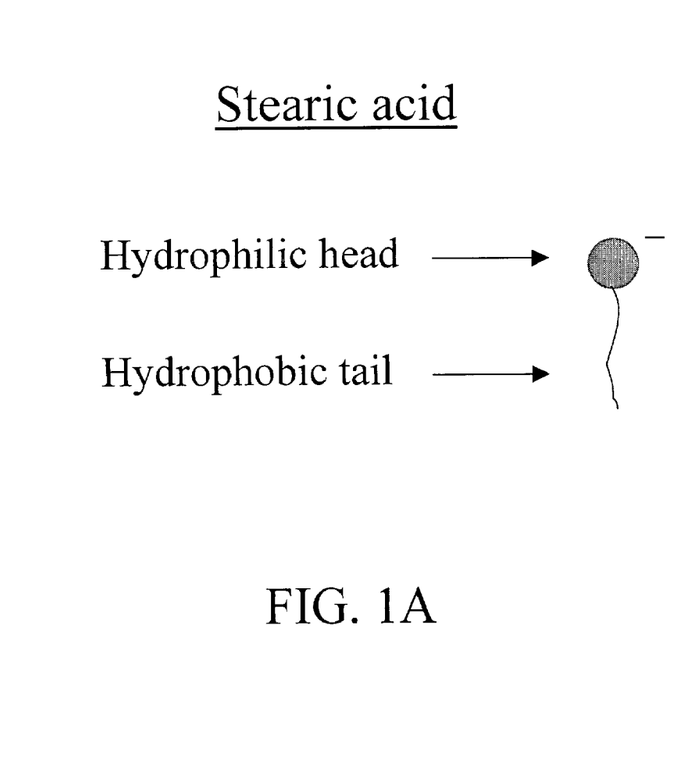
FIG. 1A shows the amphiphilic nature of stearic acid.
Figure 1B:
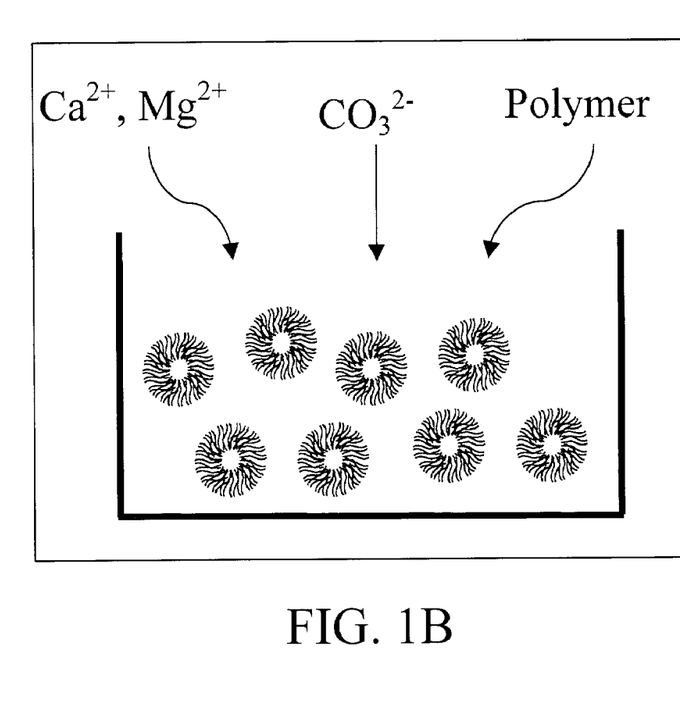
FIG. 1B shows reactants utilized to form core-shell particles of the subject invention.
Figure 1C:
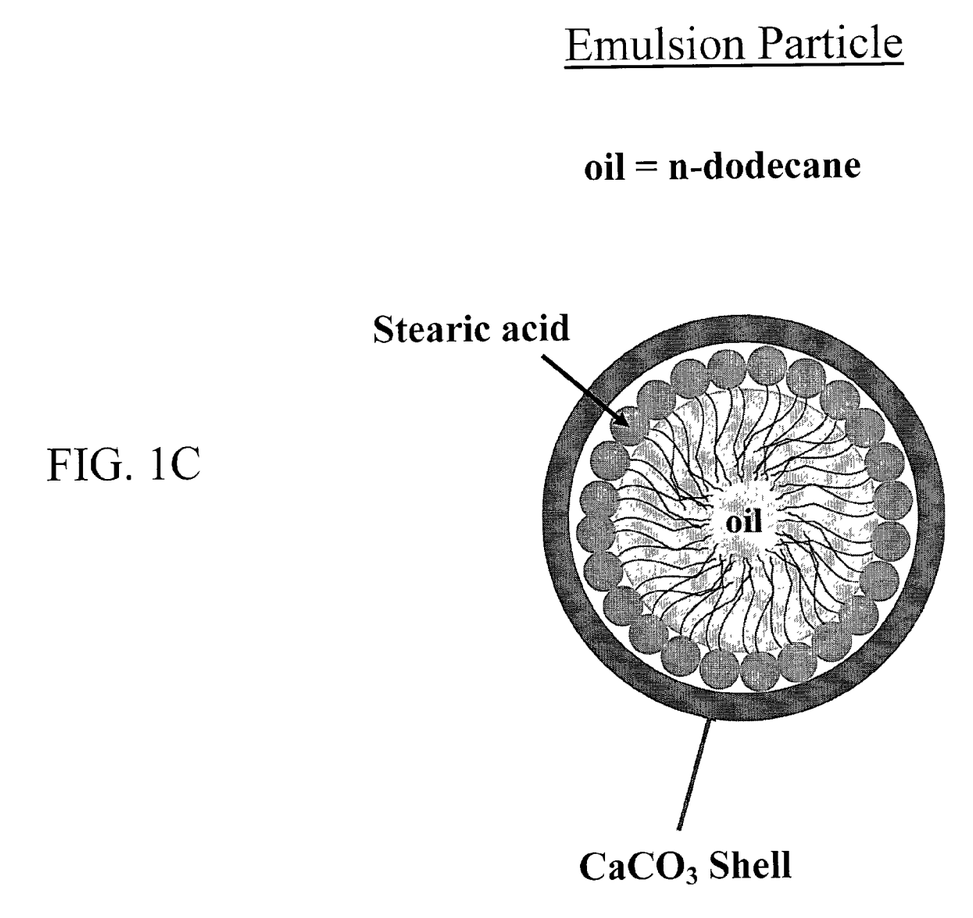
FIG. 1C shows the structure of a core-shell particle of the subject invention.
Figure 2A:
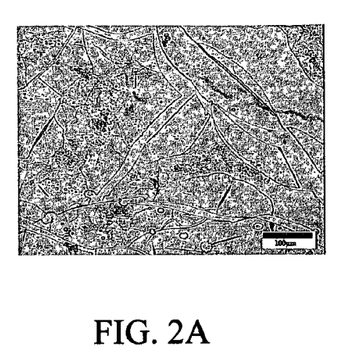
FIGS. 2A and 2B show polarized light micrographs of thin calcium carbonate films deposited under stearic acid monolayers via a PILP process. Bar=100 μm.
Figure 2B:
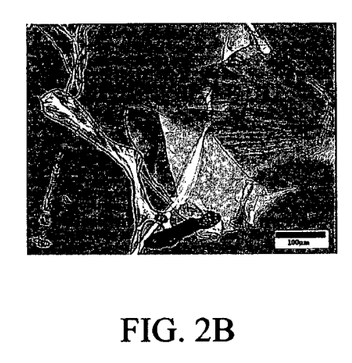

Formation of Free-Standing Films of Calcium Carbonate Under Langmuir Monolayers As a preliminary step to core-shell particle fabrication, and to better understand the deposition of calcium carbonate films on surfactant templates, the formation of freestanding films of the mineral under Langmuir monolayers spread at the air-liquid interface was investigated. FIGS. 2A and 2B show polarized light micrographs of mineral films deposited under stearic acid monolayers. The micrographs were taken using a gypsum wave plate, which renders amorphous material to appear as the same magenta color as the background. As seen by the lack of birefringence in FIG. 2A, the initial film is amorphous and optically isotropic (iso). Interestingly, the film cracked like a brittle glass when scooped onto a coverslip, which is not typical for an amorphous calcium carbonate (ACC) phase (granular ACC precipitates are produced from highly supersaturated solutions). If the films are removed from solution and let to dry in air, they crystallize in either spherulitic (sph) or single-crystalline (sc) patches (FIG. 2B). Similar results were obtained under arachidic acid monolayers.

Repeating this experiment using cholesterol or diolein surfactants, in contrast, did not yield the uniform mineral film under the monolayer. Both stearic acid and arachidic acid surfactants have partially deprotonated carboxylic acid headgroup functionalities, while cholesterol and diolein surfactants, which bear alcohol moieties, remain polar but uncharged. Therefore, the surface charge on the monolayer is thought to play an important role in attracting mineral species and the ion-binding polymer to the surface, serving to increase ion saturation, and induce the deposition of the mineral precursor.

EXAMPLE 2

Surface-Induced Deposition of a Mineral Shell onto a Charged Emulsion Droplet Using stearic acid as a surfactant, n-dodecane oil was dispersed in water to form an oil-in-water emulsion. To coat these emulsion droplets, they were first combined with $Ca^{2+}$ dissolved in aqueous solution, along with polyaspartic acid to induce the PILP process. $Mg^{2+}$ ions were also added to enhance the inhibitory action of the polymer, which helps to inhibit traditional crystal growth from solution (as opposed to from the precursor phase). The $CO_3^{2-}$ counterion was subsequently pumped into the above mixture using ultra-low-flow peristaltic pumps. To monitor its effect on mineral deposition, the surface charge on the surfactant layer was varied by adjusting the pH of the aqueous solutions between 7 and 11 ($pK_a$ of stearic acid is 10.15).

Figure 3A:
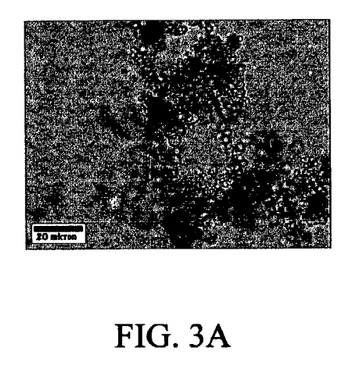
FIGS. 3A–3C show cross-polarized light micrographs with gypsum wave plate of calcium carbonate-coated emulsion droplets. Bar=200 μm.
Figure 3B:
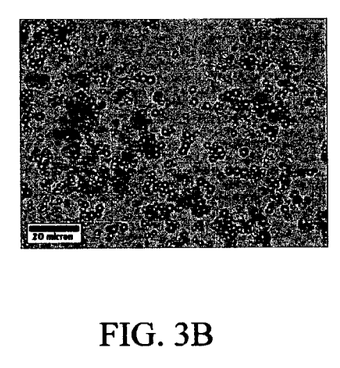
Figure 3C:
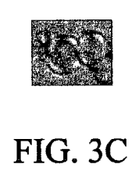

FIG. 3A shows freshly coated particles synthesized in this manner at pH 7. As detected from the lack of birefringence under cross-polarized light, the particles, as expected, initially had an amorphous $CaCO_3$ shell. After rinsing the particles with saturated $CaCO_3$ and ethanol, the particles were allowed to dry in air. FIG. 3B shows particles synthesized at pH 8 that were allowed to age in air for 1 week. The presence of birefringence in some of the spherical shells can now be detected, indicating an amorphous to crystalline phase transformation had taken place in the mineral shell, as was observed in the thin flat films. Furthermore, the Maltese cross pattern in the birefringence (see FIG. 3C, which is a magnification of FIG. 3B, lower right) indicates a spherulitic crystalline structure of the shell. The polycrystalline nature of spherulites suggests that the shell is naturally porous (without requiring patterning of the deposition process), although it is at a very fine scale since the particles appear smooth at relatively high magnification.

Figure 4A:
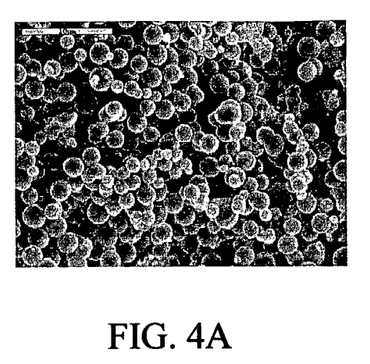
FIGS. 4A–4D show scanning electron micrographs (SEMs) (FIG. 4A–4C) of calcium carbonate-coated core-shell particles and energy dispersive spectroscopic (EDS) data (FIG. 4D). Particles in FIG. 4B were crushed by shearing between glass slides, and show the shell thickness of those particles that were fractured. Bar=10 μm in FIGS. 4A and 4B; and 2 μm in FIG. 4C.
Figure 4B:
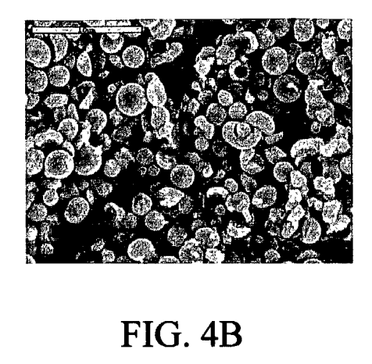
Figure 4C:
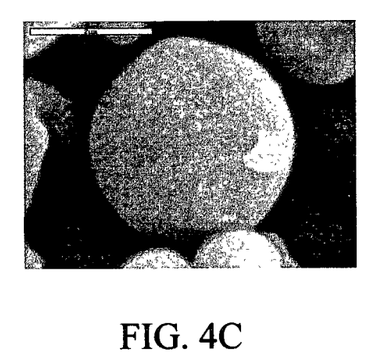
Figure 4D:
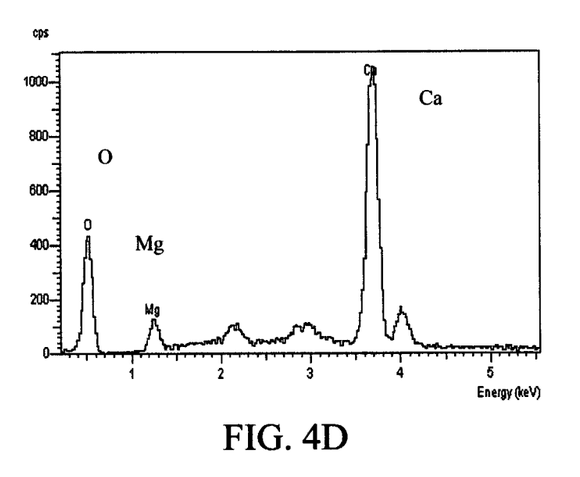

Under scanning electron microscopy (SEM), the morphology and uniformity of the particles were better judged. From these observations, particles synthesized at pH 11 yielded the best results—fairly monodisperse, uniformly spherical particles of diameter ranging between 1–5 μm (see FIG. 4A). Since the formation of a shell around the emulsion droplets was most enhanced at this pH setting, the increased surface charge at pH 11, compared to lower pHs, was deemed to be instrumental in the deposition of the PILP precursor. A sample of these particles was sheared between glass slides, and SEM of the resulting product is pictured in FIG. 4B. The presence of spherical shell fragments and hollow cores confirms the core-shell structure of the fabricated particles. The shell thickness, based on SEM images such as those shown in FIGS. 4A–4C, was observed to be between 200 and 500 nm in thickness. No specific correlation between particle diameter and shell thickness was noticed, although it is thought that by controlling the reaction time, this property might be tailorable. The shell is a smooth uniform coating (FIG. 4C), and although it appears to be spherulitic, it is not composed of an aggregation of individual crystals that nucleated from solution on the template, but rather it transformed from an amorphous precursor phase. Using Energy Dispersive Spectroscopy (FIG. 4D), the presence of Ca, Mg, and O in the particle shell was confirmed, suggesting that the mineral is a Mg-bearing $CaCO_3$ phase (which is also seen for PILP films deposited onto solid substrates).

In summary, the synthesis of core-shell particles was carried out using an oil-in-water emulsion as a substrate. The reaction chemistry was conducted at a consistent final $Ca^{2+}$ and $CO_3^{2-}$ concentration of 20 mM and 150 mM respectively, with a polymer level varied between 0 and 300 μg/ml, and a Mg level varied between 0 and 100 mM. Peristaltic pumping was employed to introduce the $CO_3^{2-}$ counterion into the reaction container. This pumping technique was utilized to synthesize core-shell particles under the following conditions: Ca/Mg=20/100 mM; $CO_3^{2-}$=150 mM; polymer=10 μg/ml; and a pH 11 environment. Since these conditions seemed to yield the best particles, further testing was conducted on particles fabricated under these conditions.

EXAMPLE 3

Deposition of Mineral Shell in Absence of PILP-Enhancing Polymer

When a PILP-enhancing polymer was not included in the reacting solution, core-shell particles could, under certain conditions, still be synthesized successfully. In some tests, the particles made without polymer were indistinguishable from those made with polymer under optical microscopy. Under SEM, however, the particles formed without polymer did not always match the quality of those made with polymer—a portion of the product was not uniformly spherical but of some modified amorphous shape. The reason these particles formed even in the absence of polymer is most likely due to the relatively high amount of Mg used (at a Ca to Mg ratio of 1 to 5). Mg is a potent crystal growth inhibitor and may have elicited a PILP-like mechanism in the formation of the shell.

A series of tests were therefore conducted, varying both the polymer and Mg levels in the synthesis procedure, to determine their effects. In the absence of Mg, no particles formed at all. Instead, polymer-modified crystals were abundant at all levels of polymer (tested between 10 and 300 μg/ml). In a second set of experiments, polymer concentration was maintained at either 10 μg/ml or 100 μg/ml, and the final concentration of Mg in the reacting solution was varied between 20 and 100 mM. In this case, core-shell particles were successfully synthesized at Mg levels as low as 20 mM, and at polymer concentrations of 10 μg/ml.

Apparently, a small amount of Mg (at 1:1 ratio of Ca/Mg) is necessary to promote the formation of a core-shell particle. However, increased polymer level significantly perturbed the process. Particles formed at Mg=80 mM and at a polymer concentration of 10 and 100 μg/ml, respectively, were compared. At 100 μg/ml, the particles formed poorly—without uniformity in shape or sizes, while the lower polymer samples formed normally. This trend held true at every Mg level tested (20, 40, 60, and 80 mM)—the particles with higher polymer doses did not form as well as with lower polymer doses. Since more polymer is likely to better inhibit mineral nucleation, the higher doses may not have allowed a shell to deposit or solidify very well on the emulsion droplet. In addition, because of the charge associated with the acidic polymer (especially at the pH 11 condition of the experiment), the high polymer level may have compromised the stability or function of the emulsion droplet.

EXAMPLE 4

Degradability of Particles Synthesized Using PILP and PILP-Enhancing Polymer

Because the shells of the core-shell particles are generated via PILP, they are in a metastable amorphous state. This suggests that the particle shells are susceptible to biodegradation once reintroduced into the blood. This is considered an important advantage of a $CaCO_3$ core-shell particle for use in drug detoxification, as it facilitates the removal of particle components from the blood stream. To determine whether these particles are indeed degradable, samples of dried particles were dispersed in buffered saline solutions, and monitored for several weeks. The particles were continually stirred while in solution to simulate the constant agitation expected if they were flowing within the circulatory system.

Particles dispersed in phosphate buffered saline solutions (PBS) (pH ~7.4) at a concentration of approximately 4 mg/mL of and 16 mg/mL lost their spherical shape due to dissolution as early as a week after dispersion, and the remaining material eventually recrystallized into several crystal morphologies. "Concentration" in this case is defined as mg of particles per mL of solution (saline, blood, etc.), and the tested concentrations are within the range that is proposed for detoxification of an overdosed patient. While the particle shell is degradable, the component materials remained as insoluble precipitates if not sufficiently diluted. In the blood stream, the reprecipitation is less likely since the larger volume will dilute the ionic species created during particle degradation.

EXAMPLE 5

Drug-Uptake Efficiency of Particles Synthesized Using PILP and PILP-Enhancing Polymer To determine whether these particles were capable of uptaking lipophilic drugs, High Performance Liquid Chromatography (HPLC) was employed. The test drug used for these studies was amitriptyline (AMT). AMT is the most widely prescribed tricyclic anti-depressant (TCA) in the United States. The drug is a significant cause for hospitalizations due to toxicity and has been reported as the most common cause of drug related deaths and suicide. Other drugs in this class include clomipramine, desipramine, imipramine, norclomipramine, nortriptyline, and trimipramine, but AMT is more typically prescribed. AMT is a highly lipophilic drug and is thought to effectively treat depression by blocking the physiological inactivation of biogenic amines.

Particles were introduced into saline solutions isotonic to blood at concentrations of 0.01%, 0.025%, and 0.05% (1%=1 mg particles/10 mL solution). AMT was then added and concentrated to 1 mM in the mixture. That mixture was sonicated for 5 minutes and then filtered by centrifugation for 30 minutes, during which time the particles were presumably absorbing the AMT. The amount of AMT remaining in the resulting filtrate was then assessed by HPLC.

Three different samples were tested for comparison purposes. The first sample was dried core-shell particles containing the oily core. The second sample was core-shell particles that were calcined at 240° C. for 1.5 hours while simultaneously vacuum dried to evaporate any n-dodecane oil in or on the particle (b.p. of n-dodecane=216° C.). From optical microscopy observations, the structure of these treated core-shell particles remained unaffected. The third sample was commercial $CaCO_3$ obtained from SIGMA-ALDRICH (mostly calcite crystals). The hypothesis was that particles with oil would absorb significantly larger amounts of AMT from solution than both particles without oil and the commercial calcite samples, since the advantage of partitioning the lipophilic molecules into the oily core was not available to the latter two.

Figure 5:
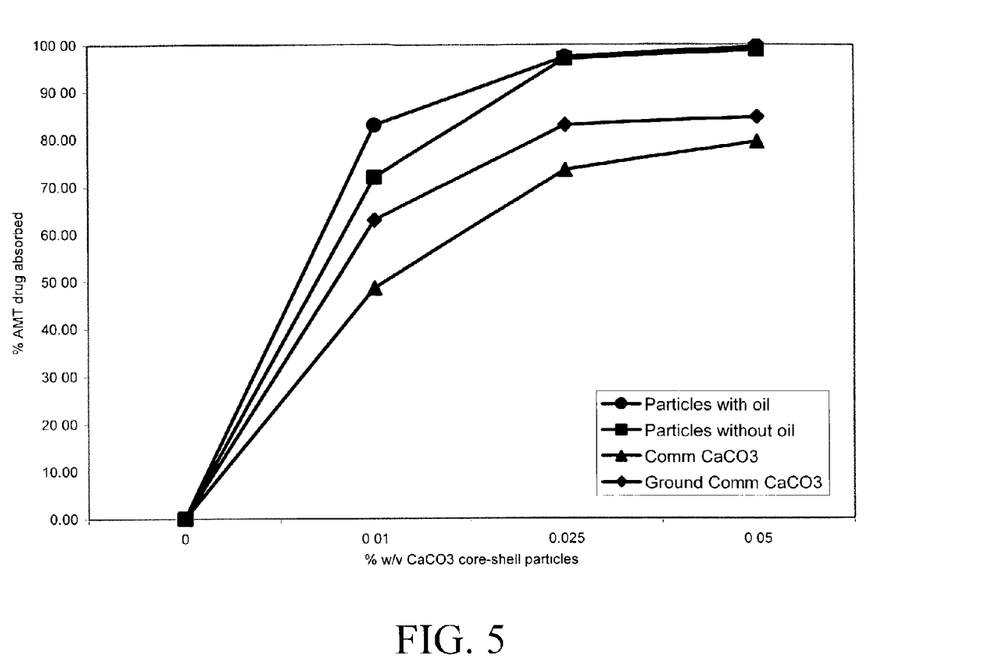
FIG. 5 shows in vitro uptake of amitriptyline (AMT) by $CaCO_3$ coated core-shell particles from saline solutions.

Results of this uptake study are shown in FIG. 5. The particles with oil were shown to extract 83% of AMT at the lower particle concentrations and upwards of 97% at 0.025% and 0.05% w/v levels. Surprisingly, the particles without oil were able to extract just as much drug as the oil-filled particles at the 0.025% and 0.05% levels, and only 10% less at 0.01%. While the commercial $CaCO_3$ did absorb the least amount of AMT, the quantity of drug that was extracted from solution was also unexpectedly high (as high as 50%). The commercial crystals used in this last sample measured as large as 40 μm, and therefore the sample's surface area did not compare well to particle samples tested. Therefore, a fourth sample was tested for drug uptake—that of commercial $CaCO_3$ crystals that were mill ground for 18 hours to reduce the crystal size, and therefore increase the surface area, to a range comparable to the particles samples. In this case, the sample was able to uptake up to 85% of the AMT drug, as shown in FIG. 5. In light of this, it is feasible that nano-scale $CaCO_3$ crystals could uptake over 90% of AMT from saline solutions. This is an important finding as it suggests that the partitioning the drug into the oily core of the particle may not be the most prevalent mechanism of drug uptake as initially thought. The drug may also be adsorbing significantly to the particle or crystal surfaces.

EXAMPLE 6

Drug Detoxification Using Calcium Carbonate Core-Shell Particles

The core-shell particles of the subject invention are particularly useful for the detoxification of lipophilic drugs within a patient in need of such detoxification. In one embodiment, an effective amount of core-shell particles are administered to the patient, such as through intravenous injection, wherein the unbound lipophilic drug (e.g., unbound to blood protein) is simply absorbed through the calcium carbonate shell of the particles, and into their core, effectively partitioning the lipophilic drug from the patient's bloodstream, for example. The particles can then be allowed to degrade, releasing the lipophilic drug over a period of time that is not harmful to the patient. Alternatively, the particles can be retrieved from the patient using known methods of particulate retrieval. In another embodiment, one or more drug-detoxifying enzymes (also referred to herein as a drug-detoxifying system) are incorporated within, or otherwise associated with, the particles of the subject invention. In another embodiment, compounds which act as inducers of endogenous drug detoxifying enzymes can be incorporated within, or otherwise associated with, the particles of the subject invention.

Drug biotransformation usually involves two phases, phase I and phase II. Phase I reactions are classified typically as oxidations, reductions, or hydrolysis of the parent drug. Following phase I reactions, the metabolites are typically more polar (hydrophilic), which increases the likelihood of their excretion by the kidney. Phase I metabolic products may be further metabolized. Phase II reactions often use phase I metabolites that can catalyze the addition of other groups, e.g., acetate, glucuronate, sulfate, or glycine to the polar groups present on the intermediate. Following phase II reactions, the resultant metabolite is typically more readily excreted. The drug detoxifying enzymes utilized in the subject invention can catalyze phase I reactions, phase II reactions, or both phase I and phase II reactions, for example.

Most phase I reactions are catalyzed by the cytochrome P450 (CYP) enzyme system, which is a superfamily consisting of heme-containing isozymes (van der Weide and, J. and Steijns, L., "*Cytochrome P450 Enzyme System: Genetic Polymorphisms and Impact on Clinical Pharmacology*", *Ann. Clin. Biochem.*, 36:722–729, 1999). At least 74 CYP gene families, of which 14 are ubiquitous in all mammals, have been described thus far (Nelson, D. R. et al., "*P450 Superfamily: Update on New Sequences, Gene Mapping, Accession Numbers, and Nomenclature*", *Pharmacogenetics*, 6:1–42, 1996). The enzymes belonging to the families CYP1, CYP2, and CYP3 catalyze the oxidative biotransformation of exogenous compounds, including many drugs, (pro)carcinogens, (pro)-mutagens, and alcohols. Other CYP families are involved in the metabolism of endogenous substances, such as fatty acids, prostaglandins, and steroid and thyroid hormones. Specific catalytic activities that have been observed with regard to some P450 isoforms in in vitro assays include testosterone 6-hydroxylase activity of CYP3A4, dextromethorphan O-deethyolase activity of CYP2D6, tolbutamide 4-hydroxylase activity of CYP2C9, phenacitin O-deethylase activity of CYP1A2, (S)-Mephenytoin 4'-hydroxylase activity of CYP2C19, chorozoxazone 6-hydroxylase activity of CYP2E1, coumarin 7-hydroxylase activity of CYP2A6, lauric acid 12-hydroxylase activity of CYP4A11, and paclitaxel 6-hydroxylase activity of CYP2C8. As indicated above, one or more P450 enzymes can be incorporated within, or otherwise associated with the particles of the subject invention. Alternatively, inducers of endogenous P450 enzyme activity can be incorporated within, or otherwise associated with, the particles of the present invention. For example, there are over twenty different CYP enzymes within the human body, with at least six of the enzymes (CYP1A2, CYP2C9, CYP2C19, CYP2D6, CYP2E1, and CYP3A) accounting for the metabolism of nearly all clinically useful medications. Examples of P450 enzymes and their corresponding substrate specificities are listed in Table 1.

TABLE 1

Examples of Cytochrome P450 (CYP) Enzymes and Corresponding Substrates

| Enzyme | Substrates |
|---|---|
| CYP1A2 | caffeine, clozapine, fluvoxamine, haloperidol, paracetamol, theophylline, acetominophen, amitriptyline, antipyrine, clomipramine, enoxacin, imipramine, olanzapine, ondansetron, phenacetin, propranolol, tacrine, R(-)warfarin, verapamil |
| CYP2A6 | coumarin |
| CYP286 | cyclophosphamide |
| CYP2C8 | arachidinic acid, paclitaxel, retinoic acid, warfarin |
| CYP2C9 | cyclophoshamide, diclofenac, hexobarbital, ibuprofen, mefanamic acid, naproxen, phenytoin, piroxicam, tenoxicam, thiotepa, tolbutamide, TCAs, torsemide, S(-)warfarin |
| CYP2C19 | amitriptyline, clomipramine, diazepam, heoxbarbital, imipramine, lansoprozole, mephenytoin, mephobarbital, melobemide, omeprazole, proguamil, -propranolol |
| CYP2D6 | antiarrhythmics such as encainide, flecainide, mexiletine, propafenone; antipsychotics such as clozapine haloperidol, perphenazine, reduced haloperidol, risperidone, thioridazine; beta-blockers such as bufuralol, metoprolol, propranolol, timolol; opiates such as codeine, dextromethorphan, hydromorphone, methadone, oxycodone, tramadol; TCAs such as amitriptyline, clomipramine, desipramine, imipramine, norelomipramine, nortriptyline, trimipramine; SSRIs such as fluoxetine, paroxetine; miscellaneous antidepressants such as maprotiline, nefazodone, venlafaxine; antihypertensives; debrisoquin; methienedioxymethamphetamine (Ecstasy); ondansetron; phenformin; sparteine; tacrine; terfenadine; tropisetron; verapamd |
| CYP2E1 | acetominophen, chlorzoxazone, ethanol, enflurane, halothane, acetone, paracetarnol |
| CYP3A4 | antiarrhythmics such as amiodarone, lidocaine, propafenone, quinidine; antidepressants such as bupropion, sertraline, TCAs (amitriptyline, clomipramine, desipramine, imipramine, norciomipramine, nortriptyline, trimipramine), venlafaxine; benzodiazepines such as aiprazolam, diazepam, midazolam, triazolam; calcium channel blockers such as diltiazem, felodipine, nifedipine, nimodipine, nisoldipine, verapamil; nonsedating antihistamines such as astemizole, terfenadine; acetaminophen; alfentanil; amiodarone; codeine; cyclosporin MG; carbamazepine; cyclophosphomide; cortisol; |

TABLE 1-continued

Examples of Cytochrome P450 (CYP) Enzymes and Corresponding Substrates

| Enzyme | Substrates |
|---|---|
| | dapsone; dexamethasone; dextromethorphan; doxorubicin; erythromycin (N-CH3); ethinylestradial etoposide; fentanyl; felodipine; ifosfamide; lansoprozole; lidocaine; lomustine; lavastatin; omeprazole; ondansetron; progesterone; tamoxifen; taxol; testosterone; triacetyloleandomycin (TAO); vincristine; vinblastine; vinorebine; warfarin; methadone |

Note: SSRIs = selective serotonin reuptake inhibitors; TCAs = tricyclic antidepressants The drug-detoxifying enzyme can be contained within the core of the core-shell particles or otherwise associated with the particles. For example, the drug-detoxifying enzyme can be adsorbed onto the calcium carbonate shell of the particles.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A core-shell particle comprising:
   (a) a shell, wherein said shell comprises a continuous calcium carbonate film that is not an aggregate of individual calcium carbonate crystals;
   (b) a core; and
   (c) an intermediate layer between said shell and said core, wherein said intermediate layer comprises an amphiphilic compound, and wherein said core and said intermediate layer are surrounded by said shell.

2. The core-shell particle of claim 1, wherein said core is hollow.

3. The core-shell particle of claim 1, wherein said core comprises a lipophilic liquid.

4. The core-shell particle of claim 3, wherein said lipophilic liquid is an oil.

5. The core-shell particle of claim 4, wherein said oil comprises dodecane.

6. The core-shell particle of claim 3, wherein said lipophilic liquid is selected from the group consisting of cyclohexane, n-hexane, benzene, cottonseed oil, rapeseed oil, squalane, squalene, waxes, styrene, divinylbenzene, butyl acrylate, 2-ethylhexyl acrylate, cyclohexyl acrylate, decyl acrylate, lauryl acrylate, dodecenyl acrylate, myristyl acrylate, palmityl acrylate, hexadecenyl acrylate, stearyl acrylate, octadecenyl acrylate, behenyl acrylate, butyl methacrylate, 2-ethylhexyl methacrylate, cyclohexyl methacrylate, decyl methacrylate, lauryl methacrylate, dodecenyl methacrylate, myristyl methacrylate, palmityl methacrylate, hexadecenyl methacrylate, stearyl methacrylate, octadecenyl methacrylate, behenyl methacrylate, and silicone macromonomers.

7. The core-shell particle of claim 1, wherein said amphiphilic compound has a partially deprotonated carboxylic acid headgroup functionality.

8. The core-shell particle of claim 1, wherein said amphiphilic compound is selected from the group consisting of stearic acid and arachidic acid.

9. The core-shell particle of claim 1, wherein said intermediate layer comprises a film of said amphiphilic compound.

10. The core-shell particle of claim 1, wherein said intermediate layer comprises a monolayer of said amphiphilic compound.

11. The core-shell particle of claim 1, wherein said shell is porous.

12. The core-shell particle of claim 1, wherein said shell has a diameter within the range of about 1 µm to about 100 µm in diameter.

13. The core-shell particle of claim 1, wherein said shell has a diameter within the range of about 1 µm to about 50 µm in diameter.

14. The core-shell particle of claim 1, wherein said shell has a diameter within the range of about 1 µm to about 5 µm in diameter.

15. The core-shell particle of claim 1, wherein said shell has a thickness within the range of about 200 nm to about 500 nm in thickness.

16. The core-shell particle of claim 1, wherein said shell has a thickness within the range of about 100 nm to about 1000 nm in thickness.

17. The core-shell particle of claim 1, wherein said intermediate layer comprises stearic acid.

18. The core-shell particle of claim 1, wherein said shell is a sphere.

19. The core-shell particle of claim 1, wherein said core and said intermediate layer are together an emulsion.

20. The core-shell particle of claim 1, wherein said core comprises a biologically active agent.

21. The core-shell particle of claim 3, wherein said core further comprises a biologically active agent.

22. The core-shell particle of claim 20, wherein said biologically active agent is selected from the group consisting of medicaments, vitamins, and mineral supplements.

23. The core-shell particle of claim 20, wherein said biologically active agent is selected from the group consisting of antifungal agents, antibacterial agents, anti-viral agents, anti-parasitic agents, growth factors, angiogenic factors, anaesthetics, mucopolysaccharides, metals, antibodies, antibody fragments, and cells.

24. The core-shell particle of claim 20, wherein said biologically active agent is a lipophilic drug.

25. The core-shell particle of claim 24, wherein said lipophilic drug comprises a tricyclic anti-depressant selected from the group consisting of amitriptyline, clomipramine, desipramine, imipramine, norclomipramine, nortriptyline, and trimipramine.

26. The core-shell particle of claim 1, wherein said core comprises a catabolic enzyme.

27. The core-shell particle of claim 3, wherein said core further comprises a catabolic enzyme.

28. The core-shell particle of claim 27, wherein said catabolic enzyme is a cytochrome P450 enzyme.

29. The core-shell particle of claim 28, wherein said cytochrome P450 enzyme is selected from the group consisting of CYP1A2, CYP2A6, CYP286, CYP2C8, CYP2C9, CYP2C19, CYP2D6, CYP2E1, and CYP3A4.

30. The core-shell particle of claim 1, wherein said continuous calcium carbonate film has a uniform thickness.

31. The core-shell particle of claim 1, wherein said continuous calcium carbonate film has a spherulitic crystal structure.

32. The core-shell particle of claim 1, wherein said continuous calcium carbonate film has a spherulitic crystalline structure that exhibits a Maltese Cross extinction pattern when viewed under cross-polarized light microscopy.

33. The core-shell particle of claim 32, wherein said continuous calcium carbonate film has a uniform thickness.

34. The core-shell particle of claim 1, wherein said continuous calcium carbonate film is smooth.

35. A core-shell particle comprising:
(a) a shell, wherein said shell comprises a continuous calcium carbonate film, wherein said film is not an aggregate of individual calcium carbonate crystals, wherein said film is formed by a liquid phase calcium carbonate precursor that confers on said film a uniform thickness and an amorphous or spherulitic crystalline structure, and wherein said spherulitic crystalline structure exhibits a Maltese Cross extinction pattern when viewed under cross-polarized light microscopy;
(b) a core; and
(c) an intermediate layer between said shell and said core, wherein said intermediate layer comprises an amphiphilic compound, and wherein said core and said intermediate layer are surrounded by said shell.

* * * * *

UNITED STATES PATENT AND TRADEMARK OFFICE
CERTIFICATE OF CORRECTION

PATENT NO. : 7,090,868 B2  
APPLICATION NO. : 10/243340  
DATED : August 15, 2006  
INVENTOR(S) : Laurie B. Gower et al.

Page 1 of 1

It is certified that error appears in the above-identified patent and that said Letters Patent is hereby corrected as shown below:

Title page, second column  
"Assistant Examiner—Lora E Barnhart" should read --Assistant Examiner—Lora E Barnhart (74) Attorney, Agent, or Firm—Saliwanchik, Lloyd & Saliwanchik--.

Column 18, line 60 (Table 1)  
"paracetarnol" should read --paracetamol--.

Column 18, line 63 (Table 1)  
"imipramine, norciomipramine" should read --imipramine, norclomipramine--.

Column 18, line 64 (Table 1)  
"such as aiprazolam" should read --such as alprazolam--.

Column 18, line 68 (Table 1):  
"cyclosporin MG" should read --cyclosporin A/G--.

Signed and Sealed this

Sixth Day of February, 2007

JON W. DUDAS  
*Director of the United States Patent and Trademark Office*